United States Patent [19]

Haga et al.

[11] Patent Number: 4,902,832
[45] Date of Patent: Feb. 20, 1990

[54] 2-SUBSTITUTED PHENYL-4,5,6,7-TETRAHYDRO-2H-ISOINDOLE-1,3-DIONES, AND THEIR PRODUCTION AND USE

[75] Inventors: Toru Haga; Eiki Nagano; Ryo Yoshida, all of Hyogo; Shunichi Hashimoto, Osaka, all of Japan

[73] Assignee: Sumitomo Chemical Company, Limited, Osaka, Japan

[21] Appl. No.: 817,667

[22] Filed: Jan. 10, 1986

Related U.S. Application Data

[63] Continuation-in-part of Ser. No. 638,680, Aug. 8, 1984, Pat. No. 4,595,409.

[30] Foreign Application Priority Data

| Aug. 31, 1983 | [JP] | Japan | 58-160855 |
| Jan. 11, 1985 | [JP] | Japan | 60-003654 |
| Jan. 11, 1985 | [JP] | Japan | 60-003655 |
| Jan. 11, 1985 | [JP] | Japan | 60-003656 |

[51] Int. Cl.$^4$ .......................... C07C 149/42
[52] U.S. Cl. ................................. 564/446
[58] Field of Search ................. 564/440, 305

[56] References Cited

U.S. PATENT DOCUMENTS

| 3,235,605 | 2/1966 | Napolitano | 260/609 |
| 3,465,001 | 9/1969 | Bolhoffer et al. | |
| 3,808,230 | 4/1974 | Podesva | 548/476 |
| 3,878,224 | 4/1975 | Matsui et al. | |
| 3,954,442 | 5/1976 | Becker et al. | |
| 3,984,435 | 10/1976 | Matsui et al. | |
| 4,001,272 | 1/1977 | Goddard | |
| 4,032,326 | 6/1977 | Goddard | |
| 4,124,375 | 11/1978 | Bollinger et al. | |
| 4,157,256 | 6/1979 | Hiraga et al. | 260/48 |
| 4,292,070 | 9/1981 | Wakabayashi | 71/96 |
| 4,349,377 | 9/1982 | Durr et al. | |
| 4,431,822 | 2/1984 | Nagano et al. | |
| 4,439,229 | 3/1984 | Swithenbank | |
| 4,484,940 | 11/1984 | Nagano et al. | |
| 4,484,941 | 11/1984 | Nagano et al. | |
| 4,536,209 | 8/1985 | Jikihara | |

FOREIGN PATENT DOCUMENTS

| 0061741 | 3/1982 | European Pat. Off. |
| 0049508 | 4/1982 | European Pat. Off. |
| 0068822 | 6/1982 | European Pat. Off. |
| 0083055 | 12/1982 | European Pat. Off. |
| 0077938 | 4/1983 | European Pat. Off. |
| 0126419 | 11/1984 | European Pat. Off. |
| 7823658 | 3/1980 | France |
| 55-130954 | 10/1980 | Japan |
| 57-24355 | 2/1982 | Japan |
| 213814 | 8/1968 | U.S.S.R. |
| 2046754 | 4/1980 | United Kingdom |

OTHER PUBLICATIONS

Chemical Abstract 89:42719j.
Chemical Abstract 98:215478w.
Chemical Abstract 93:114150z.
Chemical Abstract 101:146132v.
Chemical Abstract 101:124918d.
Chemical Abstract 101:124919e.

*Primary Examiner*—Catherine L. Mills
*Attorney, Agent, or Firm*—Birch, Stewart, Kolasch & Birch

[57] ABSTRACT

A compound of the formula:

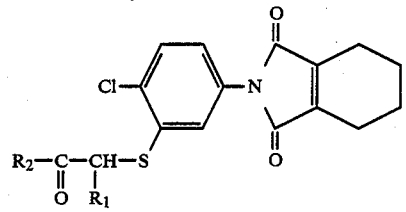

wherein $R_1$ is a hydrogen atom, a fluorine atom or a methyl group and $R_2$ is as $C_1$–$C_3$ alkyl group, a $C_1$–$C_5$ alkoxy group, a chloro($C_2$–$C_4$)alkoxy group, a dichloro($C_2$–$C_4$)alkoxy group, a cyclo($C_3$–$C_7$)alkoxy group, a phenoxy group, a $C_1$–$C_5$ alkylthio group or a di($C_1$–$C_5$)alkylamino group, which is useful as a herbicide.

1 Claim, No Drawings

2-SUBSTITUTED PHENYL-4,5,6,7-TETRAHYDRO-2H-ISOINDOLE-1,3-DIONES, AND THEIR PRODUCTION AND USE

This is a continuation-in-part application of our co-pending application Ser. No. 638,680 filed on Aug. 8, 1984 now U.S. Pat. No. 4,595,409.

The present invention relates to 2-substituted phenyl-4,5,6,7-tetrahydro-2H-isoindole-1,3-diones (hereinafter referred to as "isoindole(s)"), and their production and use.

The said isoindoles are representable by the formula:

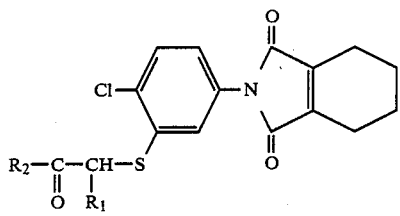

wherein $R_1$ is a hydrogen atom, a fluorine atom or a methyl group and $R_2$ is a $C_1$-$C_3$ alkyl group, a $C_1$-$C_5$ alkoxy group, a chloro($C_2$-$C_4$)alkoxy group, a dichloro($C_2$-$C_4$)alkoxy group, a cyclo($C_3$-$C_7$)alkoxy group, a phenoxy group, a $C_1$-$C_5$ alkylthio group or a di($C_1$-$C_5$)alkylamino group.

This invention also relates to intermediates in production of the isoindoles (I), and their production, said intermediates being representable by the general formula:

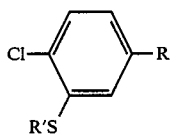

wherein R is an amino group or a 4,5,6,7-tetrahydrophthalimido group and R' is a hydrogen atom or a carboxymethyl group, provided that when R is a 4,5,6,7-tetrahydrophthalimido group, R' is a carboxymethyl group and include specifically 5-amino-2-chlorobenzenethiol of the formula:

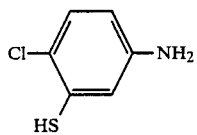

5-amino-2-chlorophenylthioacetic acid of the formula:

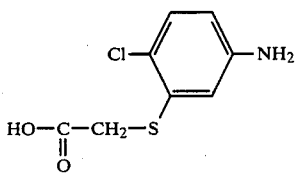

and 2-(3-carboxymethylthio-4-chlorophenyl)-4,5,6,7-tetrahydro-2H-isoindole-1,3-dione of the formula:

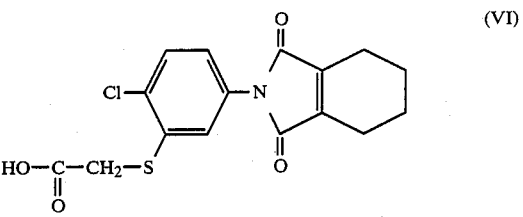

It is known that certain kinds of isoindoles are effective as herbicides. For instance, the herbicidal use of 2-(4-chlorophenyl)-4,5,6,7-tetrahydro-2H-isoindole-1,3-dione, 2-(4-chloro-3-ethoxycarbonylmethoxyphenyl)-4,5,6,7-tetrahydro-2H-isoindole-1,3-dione and 2-(4-chloro-3-ethoxycarbonylmethylaminophenyl)-4,5,6,7-tetrahydro-2H-isoindole-1,3 -dione is disclosed in U.S. Pat. No. 3,878,224, EP-No. 0049508. A and EP-No. 0077938A. However, their herbicidal effect is not necessarily satisfactory.

It has now been found that the isoindoles (I) show a strong herbicidal activity against a wide variety of weeds including broad-leaved weeds, Graminaceous weeds and Cyperaceae weeds in agricultural plowed field by foliar or soil treatment and do not produce any material phytotoxicity on various agricultural crops (i.e. corn, wheat, rice plant, soybean). Examples of broad-leaved weeds are wild buckwheat (*Polygonum convolvulus*), pale smartweed (*Polygonum lapathifolium*), common purslane (*Portulaca oleracea*), common lambsquarters (*Chenopodium album*), redroot pigweed (*Amaranthus retroflexus*), garden radish (*Raphanus sativus*), hemp sesbania (*Sesbania exaltata*), sicklepod (*Cassia tora*), velvetleaf (*Abutilon theophrasti*), prickly sida (*Sida spinosa*), field pansy (*Viola arvensis*), wild carrot (*Daucus carota*), catchweed bedstraw (*Galium aparine*), ivyleaf morningglory (*Ipomoea hederifolia*), tall morningglory (*Ipomoea purpurea*), field bindweed (*Convolvulus arvensis*), red deadnettle (*Lamium purpureum*), henbit (*Lamium amplexicaure*), jimsonweed (*Datura stramonium*), black nightshade (*Solanum nigrum*), birdseye speedwell (*Veronica persica*), ivyleaf speedwell (*Veronica hederaefolia*), heartleaf cocklebur (*Xanthium strumarium*), common sunflower (*Helianthus annuus*), scentless chamomile (*Matricaria inodola*), corn marigold (*Chrysanthemum segetum*), etc. Examples of Graminaceous weeds against which the isoindoles (I) show a herbicidal activity are Japanese millet (*Echinochloa frumentacea*), common barnyardgrass (*Echinochloa crus-galli*), green foxtail (*Setaria viridis*), large crabgrass (*Digitaria sanguinalis*), annual bluegrass (*Poa annua*), blackgrass (*Alopecurus myosuroides*), common oat (*Avena sativa*), etc. Examples of Cyperaceae weeds are rice flat sedge (*Cyperus iria*), etc. Further, they are also useful in controlling or exterminating in the paddy field the broad-leaved weeds such as barnyardgrass (*Echinochloa oryzicola*), broad-leaved weeds such as common falsepimpernel (*Lindernia procumbens*), toothcup (*Rotala indica*), waterwort (*Elatine triandra*), Cyperaceous weeds such as umbrella plant (*Cyperus difformis*), hardstem bulrush (*Scirpus juncoides*), slender spikerush (*Eleocharis acicularis*), water nutsedge (*Cyperus serotinus*) and the paddy-field weeds such as pickerelweed (*Monochoria vaginalis*), arrowhead (*Sagittaria pygmaea*), while exerting no material phytotoxicity to rice plants.

Accordingly, the isoindoles (I) can be used as herbicides applicable to agricultural plowed field as well as paddy field.

Among the isoindoles (I) of the invention, those wherein $R_1$ is a hydrogen atom and $R_2$ is a $C_1$-$C_5$ alkoxy group, a chloro($C_2$-$C_4$)alkoxy group, a dichloro($C_2$-$C_4$)alkoxy group, a cyclo($C_3$-$C_7$)alkoxy group, a phenoxy group or a $C_1$-$C_5$ alkylthio group are preferable in view of their prominent herbicidal activity as well as their scarce phototoxicity to crop plants. They hardly exert a chemical injury to soybeans and corn on foliar treatment in the plowed field.

The isoindole (I) is obtainable from 2-chloro-5-nitrobenzenesulfonyl chloride (V) [P. Fischer: Ber., Vol.

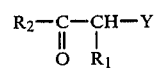

$$R_2-\underset{\underset{O}{\|}}{C}-\underset{\underset{R_1}{|}}{CH}-Y \qquad (II)$$

wherein $R_1$ and $R_2$ are each as defined above and Y is a chlorine atom, a bromine atom or an iodine atom.

The reaction is usually carried out in a solvent in the presence of a dehydrohalogenating agent with or without a phase transfer catalyst at a temperature of about 70° to 100° C. for a period of 1 to 24 hours. The amounts of the compound (II) and the dehydrohalogenating agent may be respectively from 1 to 5 equivalents and from 1 to 10 equivalents to the compound (III).

Examples of the solvent are aliphatic hydrocarbons

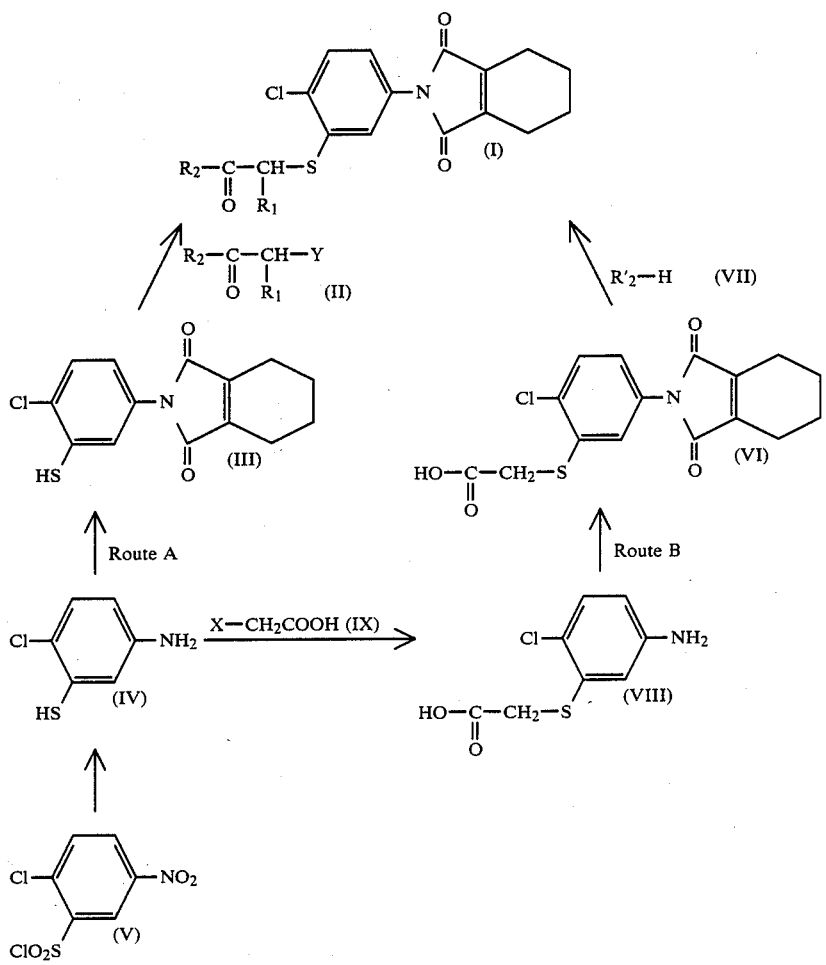

wherein $R_1$ and $R_2$ are each as defined above and $R_2'$ is a $C_1$-$C_5$ alkyloxy group, a chloro($C_2$-$C_4$)alkyloxy group, a dichloro($C_2$-$C_4$)alkyloxy group or a cyclo($C_3$-$C_7$)alkyloxy group and X and Y are each a chlorine atom, a bromine atom or an iodine atom.

The above reactions are explained further in detail below.

Route A

The isoindole (I) is obtainable by reacting 2-(4-chloro-3-hydrothiophenyl)-4,5,6,7-tetrahydro-2H-isoindole-1,3-dione, i.e. the compound (III), with a compound of the formula:

(e.g. hexane, heptane, ligroin), aromatic hydrocarbons (e.g. benzene, toluene, xylene), halogenated hydrocarbons (e.g. dichloroethane, chlorobenzene, dichlorobenzene), ethers (e.g. diisopropyl ether, dioxane, diethylene glycol dimethyl ether), ketones (e.g. acetone, methyl ethyl ketone, methyl isobutyl ketone, isophorone, cyclohexanone), nitriles (e.g. acetonitrile, isobutyronitrile), acid amides (e.g. formamide, N,N-dimethylformamide, acetamide), sulfur compounds (e.g. dimethylsulfoxide, sulfolane), water. They may be used alone or in combination. Examples of the dehydrohalogenating agents are organic bases (e.g. pyridine, triethylamine, N,N-diethylaniline), inorganic bases (e.g. sodium hydroxide, potassium hydroxide, sodium carbonate, potassium carbonate, sodium hydride), alkali metal alkoxides (e.g. sodium methoxide, sodium ethoxide), etc. As the phase transfer catalyst, there may be used tetra-n-butylammonium bromide, benzyltri-n-butylammonium chloride, etc.

The reaction mixture may be subjected to ordinary post-treatment such as extraction or condensation to recover the produced isoindole (I). When desired, the product may be further purified by a per se conventional procedure such as column chromatography or recrystallization.

For production of the compound (III), 2-chloro-5-nitrobenzenesulfonyl chloride, i.e. the compound (V), is first reacted with stannous chloride and hydrochloric acid or with zinc and hydrochloric acid or sulfuric acid at a temperature of 40° to 100° C. to give 2-chloro-5-aminothiophenol, i.e. the compound (IV). The amount of the stannous chloride or zinc is usually from 6 to 10 equivalents to the compound (V).

After completion of the reaction, the reaction mixture is subjected to post-treatment, for instance, addition of conc. hydrochloric acid and collection of the precipitate. If necessary, the collected product may be further purified by a per se conventional procedure such as chromatography or recrystallization.

Then, the compound (IV) is reacted with 1 to 3 equivalents of 3,4,5,6-tetrahydrophthalic anhydride in a solvent at a temperature of 90 to 120° C. for a period of 1 to 24 hours. As the solvent, there may be employed aliphatic hydrocarbons (e.g. hexane, ligroin), aromatic hydrocarbons (e.g. benzene, toluene, xylene), ethers (e.g. diisopropyl ether, dioxane, diethylene glycol dimethyl ether), aliphatic acids (e.g. acetic acid, propionic acid), water, or a mixture thereof.

After completion of the reaction, the reaction mixture is subjected to ordinary post-treatment such as extraction, condensation or precipitation. The thus obtained product may be, if necessary, purified by a per se conventional procedure such as column chromatography or recrystallization.

Typical examples of production of the isoindoles (I) as well as their intermediates via Route A are as follows:

EXAMPLE 1

Production of the compound (I)

A suspension of 2-(4-chloro-3-hydrothiophenyl)-4,5,6,7-tetrahydro-2H-isoindole-1,3-dione (1.5 g) and tetra-n-butylammonium bromide (0.2 g) in a 5% potassium hydroxide solution (9 ml) was heated to 80° to 90° C., and 2,2-dichloroethyl bromoacetate (3.5 g) was dropwise added thereto at 80° to 90° C. The resultant mixture was heated at the same temperature for 1 hour and allowed to cool. The reaction mixture was diluted with water and extracted with toluene. Toluene was removed under reduced pressure, and the residue was purified by silica gel column chromatography using a mixture of ethyl acetate and n-hexane (1:4) as an eluent to give 0.6 g of 2-[4-chloro-3-(2,2-dichloroethyloxycarbonylmethylthio)phenyl]-4,5,6,7-tetrahydro-2H-isoindole-1,3-dione. $n_D^{28.0}$ 1.5897.

In the same manner as above, there were produced other isoindoles (I), of which typical examples are as shown in Table 1.

TABLE 1

(I) Structure: 4-chloro-phenyl (with $R_2-\underset{\underset{O}{\|}}{C}-\underset{\underset{R_1}{|}}{CH}-S$ substituent) attached to N of 4,5,6,7-tetrahydro-2H-isoindole-1,3-dione

| Compound No. | $R_1$ | $R_2$ | Physical constant |
|---|---|---|---|
| 1 | H | Cl$_2$CHCH$_2$O | $n_D^{28.0}$ 1.5897 |
| 2 | H | ClCH$_2$CH$_2$O | $n_D^{29.7}$ 1.5987 |
| 3 | H | n-C$_5$H$_{11}$O | $n_D^{30.5}$ 1.5482 |
| 4 | H | iso-C$_3$H$_7$O | $n_D^{30.5}$ 1.5932 |
| 5 | CH$_3$ | n-C$_4$H$_9$(CH$_3$)N | $n_D^{29.7}$ 1.5538 |
| 6 | CH$_3$ | n-C$_5$H$_{11}$S | $n_D^{30.5}$ 1.5682 |
| 7 | H | iso-C$_3$H$_7$S | $n_D^{30.5}$ 1.5932 |
| 8 | H | cyclopentyl-O | $n_D^{29.7}$ 1.5785 |
| 9 | H | C$_2$H$_5$O | $n_D^{25.7}$ 1.5758 |
| 10 | H | CH$_3$O | m.p., 106.3° C. |
| 11 | H | cyclohexyl-O | $n_D^{20.4}$ 1.5784 |
| 12 | H | C$_6$H$_5$O | m.p., 120.1° C. |
| 13 | H | CH$_3$ | m.p., 166.5° C. |
| 14 | F | C$_2$H$_5$O | $n_D^{19.2}$ 1.5871 |

EXAMPLE 2

Production of the compound (III)

2-Chloro-5-aminobenzenethiol (21.1 g) and tetrahydrophthalic anhydride (20.4 g) were dissolved in acetic acid (130 ml), and the resultant mixture was heated at 100° to 110° C. for 1 hour while stirring. The reaction mixture was allowed to cool and diluted with water. The precipitated crystals were collected by filtration and washed with ethanol to give 28.2 g of 2-(4-chloro-3-hydrothiophenyl)-4,5,6,7-tetrahydro-2H-isoindole-1,3-dione. m.p., 153°–155° C.

EXAMPLE 3

Production of the compound (IV)

A solution of anhydrous stannous chloride (152.5 g) in conc. hydrochloric acid (150 ml) was cooled to 0° C., and 2-chloro-5-nitrobenzenesulfonyl chloride (34.3 g) was added thereto while stirring. The resultant mixture was heated at 100° C. for 15 minutes while stirring, followed by being allowed to stand. Conc. hydrochloric acid (230 ml) was added to the reaction mixture. The precipitated crystals were collected by filtration, neutralized with a 4% aqueous sodium carbonate solution and extracted with ethyl acetate. The organic layer was dried and concentrated to give 25.0 g of 2-chloro-5-aminothiophenol.

NMR (CDCl$_3$+D$_6$-DMSO)δppm: 4.0 (3H, br, NH$_2$, SH), 6.3–6.7 (2H, m), 6.8–7.1 (1H, m).

Route B

The isoindole (I) wherein $R_1$ is a hydrogen atom is obtainable by reacting 2-(3-carboxymethylthio-4-chlorophenyl)-4,5,6,7-tetrahydro-2H-isoindole-1,3-dione, i.e. the compound (VI), with 1 equivalent to a large excess amount, preferably 1 to 3 equivalents, of an alcohol of the formula:

$$R'_2\text{—H} \qquad \text{(VII)}$$

wherein $R_2'$ is as defined above, optionally in a solvent (e.g. benzene, toluene, xylene, monochlorobenzene), in the presence of a catalytic amount of an acid such as p-toluenesulfonic acid hydrate at a temperature of 80° C. to the boiling temperature of the solvent or the alcohol (VII) for a period of 0.5 to 10 hours, during which the by-produced water is eliminated from the reaction system by the aid of molecular sieve 3A or Dean Stark's trap.

After completion of the reaction, the reaction mixture may be admixed with water and subjected to ordinary post-treatment such as solvent extraction or condensation to recover the produced isoindole (I). When desired, the product may be further purified by a per se conventional procedure such as column chromatography or recrystallization.

For production of the compound (VI), the compound (V) is first reacted with stannous chloride and hydrochloric acid or with zinc and hydrochloric acid or sulfuric acid at a temperature of 40° to 100° C. as in Route A to give the compound (IV).

The compound (IV) is then reacted with a haloacetic acid of the formula:

$$\text{X—CH}_2\text{COOH} \qquad \text{(IX)}$$

wherein X is a chlorine atom, a bromine atom or an iodine atom in a solvent in the presence of a base at a temperature of 0° to 100° C., preferably from room temperature (about 20° C.) to 60° C., within about 5 hours, followed by acidification with conc. hydrochloric acid to give 5-amino-2-chlorophenylthioacetic acid, i.e. the compound (VIII). As the base, there may be employed sodium hydroxide, potassium hydroxide, potassium carbonate, sodium hydride, etc. Examples of the solvent are water, N,N-dimethylformamide, dimethylsulfoxide, etc. In case of sodium hydride being used as the base, water should not be employed. The amounts of the compound (IX) and of the base may be respectively 1.0 to 2.0 equivalents and 2 to 5 equivalents to one equivalent of the compound (IV).

Then, the compound (VIII) thus obtained is reacted with 1.0 to 1.1 equivalents of 3,4,5,6-tetrahydrophthalic anhydride in a solvent (e.g. acetic acid, propionic acid, butyric acid) at a temperature of 100° C. to the boiling temperature of the solvent for a period of 2 to 10 hours, preferably of 3 to 6 hours to give the compound (VI).

In each of the above reactions, the reaction mixture after completion of the reaction may be subjected to conventional post-treatment to recover the product. For instance, the reaction mixture may be admixed with water, and the precipitated crystals are collected by filtration, or the resultant mixture is extracted with an organic solvent, followed by concentration. When desired, the recovered product may be purified by a per se conventional purification procedure such as chromatography or recrystallization.

Some typical examples for production of the isoindoles (I) as well as their intermediates via Route B are shown below.

EXAMPLE 4

Production of the compound (I)

2-(3-Carboxymethylthio-4-chlorophenyl)-4,5,6,7-tetrahydro-2H-isoindole-1,3-dione (3.61 g), cyclopentanol (1.24 g) and p-toluenesulfonic acid monohydrate (0.18 g) were suspended in toluene (10 ml), molecular sieve 3A (0.2 g) was added thereto, and the resultant mixture was heated under reflux for 6 hours. The reaction mixture was allowed to cool, admixed with water and extracted with toluene. The extract was washed with water, dried, and concentrated. The precipitated crystals were washed with methanol to give 1.91 g of 2-(3-cyclopentyloxycarbonylmethylthio-4-chlorophenyl)-4,5,6,7-tetrahydro-2H-isoindole-1,3-dione. m.p., 57°–59° C.

In the same manner as above but using methanol instead of cyclopentaol, there was produced 2-(3-methoxycarbonylmethylthio-4-chlorophenyl)-4,5,6,7-tetrahydro-2H-isoindole-1,3-dione. m.p., 106.3° C.

EXAMPLE 5

Production of the compound (VI)

5-Amino-2-chlorophenylthioacetic acid (11.0 g) and 3,4,5,6-tetrahydrophthalic anhydride (8.6 g) were suspended in acetic acid (44 ml), and the suspension was heated under reflux for 5 hours. The reaction mixture was allowed to cool, admixed with water and extracted with ethyl acetate. The extract was washed with water, dried and concentrated to give 8.7 g of 2-(3-carboxymethylthio-4-chlorophenyl)-4,5,6,7-tetrahydro-2H-isoindole-1,3-dione. m.p., 162°–163° C.

EXAMPLE 6

Production of the compound (VIII)

5-Amino-2-chlorobenzenethiol (13.0 g) and bromoacetic acid (12.1 g) were suspended in a 10% aqueous sodium hydroxide solution (87 ml), and the suspension was heated at 90° C. for 1 hour. The reaction mixture was allowed to cool, adjusted to pH 4 with conc. hydrochloric acid and extracted with ethyl acetate. The extract was washed with water and concentrated. The residue was crystallized from ether to give 11.0 g of 5-amino-2-chlorophenylthioacetic acid. m.p., 152°–154° C.

On the practical usage of the isoindole (I) as a herbicide, it may be applied as such or in any preparation form such as emulsifiable concentrate, wettable powder, suspension, granules, etc. in combination with a conventional solid or liquid carrier or diluent, a surface active agent and/or an auxiliary agent.

The content of the isoindole (I) as the active ingredient in said preparation form may be usually within a range of 0.03 to 90% by weight, preferably of 0.05 to 80% by weight.

Examples of the solid carrier or diluent are kaolin clay, attapulgite clay, bentonite, terra alba, pyrophyllite, talc, diatomaceous earth, calcite, walnut powders, urea, ammonium sulfate, synthetic hydrated silicon dioxide, etc. As the liquid carrier or diluent, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), soybean oil, cotton seed oil, dimethylsulfoxide, acetonitrile, water, etc. The surface active agent used for emulsification, dispersion or spreading may be any of the anionic and non-ionic type of agents. Examples of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymers, sorbitan fatty acid esters, polyoxyethylene sorbitan fatty acid esters, etc. Examples of the auxiliary agents include ligninsulfonates, alginates, polyvinyl alcohol, gum arabic, CMC (carboxymethyl cellulose), PAP (isopropyl acid phosphate), etc.

Practical embodiments of the herbicidal composition according to the invention are illustratively shown in the following examples wherein parts and % are by weight. The compound number of the active ingredient corresponds to the one in Table 1.

FORMULATION EXAMPLE 1

Thirty parts of Compound No. 1, 5 parts of calcium ligninsulfonate, 3 parts of sodium laurylsulfate and 62 parts of synthetic hydrated silicon dioxide are well mixed to obtain a wettable powder.

FORMULATION EXAMPLE 2

Ten parts of Compound No. 3, 14 parts of polyoxyethylenestyrylphenyl ether, 6 parts of calcium dodecylbenzenesulfonate, 30 parts of xylene and 40 parts of cyclohexanone are well mixed to obtain an emulsifiable concentrate.

FORMULATION EXAMPLE 3

Two parts of Compound No. 2, 1 part of synthetic hydrated silicon dioxide, 2 parts of calcium ligninsulfonate, 30 parts of bentonite and 65 parts of kaolin clay are well mixed. The mixture is then kneaded with water, granulated and dried to obtain granules.

FORMULATION EXAMPLE 4

Twenty-five parts of Compound No. 6 is mixed with 3 parts of polyoxyethylene sorbitan monooleate, 3 parts of CMC (carboxymethyl cellulose) and 69 parts of water, and the mixture is pulverized until the particle size of the mixture becomes less than 5 microns to obtain a suspension.

The isoindoles (I) thus formulated in any suitable formulation form are useful for the pre-emergence or post-emergence control of undesired weeds by soil or foliar treatment as well as flood fallowing treatment. These treatments include the application to the soil surface prior to or after the transplanting or the incorporation into the soil. The foliar treatment may be effected by spraying the herbicidal composition containing the isoindole (I) over the top of plants. It may also be applied directly to weeds with care so as to keep the chemical off the crop foliage.

The isoindoles (I) of the invention may be used together with other herbicides to improve their activity as herbicides, and in some cases, a synergistic effect can be expected. Further, they may be applied in combination with insecticides, acaricides, nematocides, fungicides, plant growth regulators, fertilizers, soil improvers, etc.

Besides, the isoindoles (I) can be used as herbicides applicable to agricultural plowed field as well as paddy field. They are also useful as herbicides to be employed for orchard, pasture land, lawn, forest, non-agricultural field, etc.

The dosage rate of the isoindoles (I) may vary on prevailing weather conditions, preparation used, prevailing season, mode of application, soil involved, crop and weed species, etc. Generally, however, the dosage rate may be from 0.05 to 50 grams, preferably from 0.2 to 20 grams, of the active ingredient per are. The herbicidal composition of the invention prepared in the form of an emulsifiable concentrate, a wettable powder or a suspension may ordinarily be employed by diluting it with water at a volume of 1 to 10 liters per are, if necessary, with addition of an auxiliary agent such as a spreading agent. Examples of the spreading agent include, in addition to the surface active agents as noted above, polyoxyethylene resin acid (ester), ligninsulfonate, abietylenic acid salt, dinaphthylmethanedisulfonate, paraffin, etc. The composition prepared in the form of granules may be normally applied as such without dilution.

The biological effect of the isoindoles (I) as herbicides will be illustratively shown in the following Examples wherein the phytotoxicity to crop plants and the herbicidal activity on weeds were observed visually as to the degree of germination as well as the growth inhibition and rated with an index 0, 1, 2, 3, 4 or 5, in which the numeral "0" indicates no material difference is seen in comparison with the untreated plant and the numeral "5" indicates the complete inhibition or death of the test plants.

The compounds shown in Table 2 below were used for comparison.

TABLE 2

| Compound No. | Chemical structure | Remarks |
| --- | --- | --- |
| A | [structure: 4-chlorophenyl attached to N of a bicyclic imide with cyclohexene fused ring] | U.S. Pat. No. 3,878,224 |
| B | [structure: F$_3$C and Cl substituted phenyl—O—phenyl with COONa and NO$_2$ substituents] | acifluorfen (Na salt; commercially available herbicide) |

TABLE 2-continued

| Compound No. | Chemical structure | Remarks |
|---|---|---|
| C | 4-Cl, 3-(C$_2$H$_5$OCCH$_2$O-)phenyl attached to N of 3,4,5,6-tetrahydrophthalimide; ester C=O | EP-0049508A |
| D | 4-Cl, 3-(C$_2$H$_5$OCCH$_2$NH-)phenyl attached to N of 3,4,5,6-tetrahydrophthalimide; amide C=O | EP-0077938A |

TEST EXAMPLE 1

Plastic pots (diameter, 10 cm; height, 10 cm) were filled with upland field soil, and the seeds of Japanese millet, wild oat, garden radish and velvetleaf were sowed therein and covered with the soil. The test plants were cultivated in a greenhouse for 10 days. Thereafter, a designed amount of the test compound formulated into an emulsifiable concentrate according to Formulation Example 2 and diluted with water containing a spreading agent was sprayed over the top to the soil surface at a spray volume of 10 liters per are by means of a small hand sprayer. After 20 days cultivation in the greenhouse, the herbicidal activity on the plants was examined. The results are shown in Table 3.

TEST EXAMPLE 2

Vats (33 cm × 23 cm × 11 cm) were filled with upland field soil and the seeds of soybean, cotton, tall morning-glory, heartleaf cocklebur, velvetleaf, common lambsquarters, corn, wheat, common barnyardgrass and green foxtail were sowed therein and the soil was covered to the depth of 1 to 2 cm. A designed amount of the test compound formulated into an emulsifiable concentrate according to Formulation Example 2 and diluted with water was sprayed to the soil surface by means of a small hand sprayer at a spray volume of 10 liters per are. After 20 days cultivation in a greenhouse, the herbicidal activity was examined. The results are shown in Table 4.

TABLE 4

| Compound No. | Dosage (g/are) | Soybean | Cotton | Tall morning-glory | Heartleaf cocklebur | velvetleaf | Common lambs-quarters | Corn | Wheat | Common barn-yard-grass | Green fox-tail |
|---|---|---|---|---|---|---|---|---|---|---|---|
| 1 | 20 | 0 | 4 | 4 | 4 | 5 | 5 | 2 | 1 | 2 | 4 |

TABLE 3

| Compound No. | Dosage (g/are) | Japanese millet | Wild oat | Garden radish | Velvet-leaf |
|---|---|---|---|---|---|
| 1 | 20 | 5 | 5 | 5 | 5 |
| 2 | 20 | 5 | 5 | 5 | 5 |
| 3 | 20 | 5 | 5 | 5 | 5 |
| 4 | 20 | 5 | 5 | 5 | 5 |
| 5 | 20 | 5 | 5 | 5 | 5 |
| 6 | 20 | 5 | 5 | 5 | 5 |
| 7 | 20 | 5 | 5 | 5 | 5 |
| 8 | 20 | 5 | 5 | 5 | 5 |
| 9 | 20 | 5 | 5 | 5 | 5 |
| 10 | 20 | 5 | 5 | 5 | 5 |
| 11 | 20 | 5 | 5 | 5 | 5 |
| 12 | 20 | 5 | 4 | 5 | 5 |
| 13 | 20 | 5 | 5 | 5 | 5 |
| 14 | 20 | 5 | 4 | 5 | 5 |
| A | 20 | 3 | 3 | 4 | 5 |

TEST EXAMPLE 3

Vats (33 cm × 23 cm × 11 cm) were filled with upland field soil and the seeds of soybean, cotton, tall morning-glory, heartleaf cocklebur, velvetleaf, common lambsquarters, corn, wheat, common barnyardgrass and green foxtail were sowed therein and cultivated in a greenhouse. A designed amount of the test compound formulated into an emulsifiable concentrate according to Formulation Example 2 and diluted with water containing a spreading agent was sprayed to the foliage of the test plants over the top by means of a small hand sprayer at a spray volume of 5 liters per are. Thereafter, the test plants were further grown in the greenhouse for 20 days, and the herbicidal activity was examined. At the time of the application, the growing stage of the test plants varied depending on their species, but they were generally at the 1 to 4 leaf stage and in 2 to 12 cm height. The results are shown in Table 5.

TABLE 5

| Compound No. | Dosage (g/are) | Soybean | Cotton | Tall morning-glory | Heart-leaf cock-lebur | Velvet-leaf | Common lambs-quaters | Corn | Wheat | Common barn-yard-grass | Green fox-tail |
|---|---|---|---|---|---|---|---|---|---|---|---|
| 1 | 1.25 | 2 | 5 | 5 | 5 | 5 | 5 | 3 | 2 | 2 | 4 |
|   | 0.32 | 0 | 5 | 5 | 5 | 5 | 5 | 1 | 0 | 1 | 2 |
| 2 | 1.25 | 2 | 5 | 5 | 5 | 5 | 5 | 2 | 1 | 2 | 3 |
|   | 0.32 | 1 | 5 | 5 | 5 | 5 | 5 | 1 | 1 | 1 | 2 |
| 3 | 1.25 | 2 | 5 | 5 | 5 | 5 | 5 | 2 | 1 | 2 | 2 |
|   | 0.32 | 1 | 5 | 5 | 5 | 5 | 5 | 1 | 1 | 1 | 2 |
| 9 | 1.25 | 2 | 5 | 5 | 5 | 5 | 5 | 3 | 1 | 2 | 0 |
|   | 0.32 | 2 | 5 | 5 | 5 | 5 | 5 | 2 | 1 | 1 | 0 |
| A | 1.25 | 1 | 2 | 3 | 2 | 5 | 5 | 1 | 0 | 1 | 0 |
|   | 0.32 | 0 | 0 | 1 | 1 | 3 | 4 | 0 | 0 | 0 | 0 |
| B | 2.5 | 2 | 2 | 5 | 4 | 2 | 5 | 0 | 1 | 2 | 1 |
|   | 0.63 | 0 | 1 | 3 | 1 | 0 | 3 | 0 | 0 | 0 | 0 |
| C | 1.25 | 2 | 5 | 4 | 4 | 5 | 5 | 1 | 1 | — | — |
|   | 0.32 | 1 | 5 | 2 | 2 | 4 | 3 | 0 | 0 | — | — |
| D | 1.25 | 4 | 5 | 5 | 5 | 5 | — | 3 | 2 | 2 | 0 |
|   | 0.32 | 3 | 5 | 3 | 3 | 5 | — | 3 | 1 | 1 | 0 |

TEST EXAMPLE 4

Cylindrical plastic pots (diameter, 8 cm; height, 12 cm) were filled with paddy field soil, and the seeds of barnyardgrass, broad-leaved weeds (e.g. common false-pimpernel, toothcup, waterwort) and hardstem bulrush and the buds of arrowhead were sowed in 1 to 2 cm depth. Water was poured therein to make a flooded condition. Rice seedlings of the 2-leaf stage were transplanted therein and grown in a greenhouse. Six days thereafter, a designed amount of the test compound formulated in an emulsifiable concentrate according to Formulation Example 2 and diluted with water (5 ml) was applied to the pots by perfusion. The test plants were grown for further 20 days in the greenhouse, and the herbicidal activity was examined. The results are shown in Table 6.

TABLE 6

| Compound No. | Dosage (g/are) | Rice plant | Barn-yard-grass | Broad-leaved weed | Hardstem bulrush | Arrow-head |
|---|---|---|---|---|---|---|
| 1 | 20 | 1 | 4 | 5 | 4 | 4 |
| 3 | 20 | 1 | 4 | 5 | 3 | 5 |

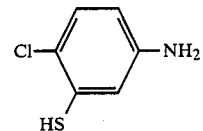

What is claimed is:

1. A compound of the formula: